US00PP08349P

United States Patent [19]

Ilsink

[11] Patent Number: Plant 8,349

[45] Date of Patent: Aug. 17, 1993

[54] MINIATURE ROSE PLANT NAMED INTERSEPT

[75] Inventor: G. P. Ilsink, Leersum, Netherlands

[73] Assignee: Interplant B.V., Leersum, Netherlands

[21] Appl. No.: 904,518

[22] Filed: Jun. 25, 1992

[51] Int. Cl.[5] ..... A01H 5/00

[52] U.S. Cl. ..... Plt./10

[58] Field of Search ..... Plt./10

*Primary Examiner*—Howard J. Locker

*Attorney, Agent, or Firm*—Christie, Parker & Hale

[57] ABSTRACT

A new variety of miniature rose plant having red flowers produced on a good pot forcing plant also suitable for growing outdoors in gardens.

2 Drawing Sheets

SUMMARY OF THE INVENTION

The present invention relates to a new and distinct variety of rose plant of the miniature rose class, which was originated by me by crossing as the seed and pollen parents unnamed and unpatented seedlings of my creation. The varietal denomination of the new variety is 'Intersept'.

Among the novel characteristics possessed by this new variety which distinguishes it from its parent and all other varieties of which I am aware is its bright red flowers borne on a plant particularly suited for production of flowering pot plants and for growing in outdoor gardens. 'Intersept' can be reproduced through propagation by cuttings, grafting, budding and micropropagation. Flowers of the new variety are long lasting on the plant. Asexual reproduction by budding, grafting and propagation of cuttings of the new variety as performed in Hazerswoude, Holland, shows that the foregoing and other distinguishing characteristics come true to form and are established and transmitted through succeeding propagations.

BRIEF DESCRIPTION OF ILLUSTRATIONS

The accompanying illustrations show typical specimens of the vegetative growth and flowers of the new variety in different stages of development depicted in color as nearly true as it is reasonably possible to make the same in a color illustration of this character. Phenotypic expression, including colors, may vary depending upon growing conditions, such as under different climate, soil, and cultivation conditions.

FIG. 1 is an illustration of a plant of the new variety of miniature rose showing flowering and growth habit; and FIG. 2 is an illustration showing details of the new miniature rose variety.

DETAILED DESCRIPTION OF THE NEW VARIETY

The following is a detailed description of my new variety, with color terminology in accordance with The Royal Horticulutral Society Colour Chart (R.H.S.C.C.) and horticultural terminology in accordance with standard terminology used in UPOV-approved horticultural guidelines. The terminology used in color descriptions herein refers to plate numbers in the aforementioned color chart.

Parentage: Seedling.

*Seed parent.*—Unnamed seedling.

*Pollen parent.*—Unnamed seedling.

Class: Miniature.

As can be seen in the accompanying illustrations, FIG. 1 shows one sample of flowering plant of 'Intersept' depicting the pot plant habit of growth and flowering. Since flowering is nearly continuous, the floriferous 'Intersept' can remain attractively in bloom for long periods when given proper care and culture.

The illustration in FIG. 2 shows details of the new variety "Intersept". In the illustration there is shown the top of a young shoot, 1; compound three, five and seven leaflet leaves, 2, 3, and 4, respectively; a stem, 5; buds, 6 and 7; a flower, 8, about one-half open; and a flower 9, fully open. Also shown are flower stems 10, 11 and 12, with reproductive organs.

The following further horticultural observations were made of specimens grown outdoors in Holland.

FLOWER

Blooming habit: Nearly continuous.

A. Bud:

(1) *Size.*—Medium.

(2) *Form.*—Ovate (before separation of sepals).

(3) *Color.*—As sepals divide, bud color is near 45A becoming near 45B to C when sepals separate.

(4) *Sepals.*—Slightly longer than bud, simple to slightly foliated.

(5) *Peduncle.*—Length — medium. Aspect — straight. Strength — erect. Color — medium green.

B. Bloom: flower: Average size for miniature.

Viewed from above.—Irregularly rounded.

Viewed from side.—(a) Upper part of fully opened flower — flat; (b) lower part of fully opened flower — flattened convex.

(1) *Size.*—Average size when fully expanded — about 3 to 4 cm.

(2) *Borne.*—Small clusters, 3 to 4 blooms, and singly.

(3) *Form.*—Ovoid to cupped at first, becoming flat; some outer petals reflex and quill to points; inner petals roll under slightly.

(4) *Petalage.*—About 20 petals under normal conditions — double.

(5) *Color.*—After sepals separate, near 45A to B; when sepals part and petals being to unfurl, color of petal tops remain near 45A to B; petals undersurface is similar near 45-45C. Open flowers show orange-yellow anthers and pollen. Coloring at point of petal attachment is near 57D. Overall tonality from a distance is bright red.

(6) *Pedicle.*—Few hairs or prickles.

(7) *Fragrance.*—Slight to none.

C. Petals:

(1) *Texture.*—Medium.

(2) *Appearance.*—Inside velvety and outside satiny.

(3) *Form and size.*—Small, obovate.

(4) *Arrangement.*—Regularly arranged, imbricated.

(5) *Petaloids in center.*—Several.

(6) *Persistence.*—Drop off cleanly.

(7) *Lasting quality.*—Long lasting quality on plant.

REPRODUCTIVE ORGANS

A. Stamens, filaments and anthers:

*Arrangement and color.*—Regularly arranged around styles; color of filaments — pale yellow.

B. Pollen:

*Color.*—Yellow orange.

C. Styles: Stigma above mouth of receptacle, pale yellow green, generally not hairy.

D. Stigmas: Positioned slightly above anthers.

E. Hips: Small, pear-shaped.

PLANT

A. Form: Bushy.

B. Growth: Vigorous.

*Average height.*—about 30 cm.

*Average spread.*—about 20 cm.

C. Foliage: Compound 3, 5 and 7 leaflets.

(1) *Size.*—Medium for a miniature.

(2) *Quantity.*—Abundant.

(3) *Color.*—Foliage at time of first flowering — light to medium green.

(4) *Shape.*—Oval, pointed.

(5) *Texture.*—Upper side has little or no gloss; underside is matte.

(6) *Edge.*—Serrate.

(7) *Serration.*—Ordinary, acumiante apices.

(8) *Leaf stem.*—Color — medium green.

(9) *Stipules.*—Short, narrow, simple, medium to light green, distinct auricle.

(10) *Leaflets.*—Cross section — slight concave, little or no undulation at margin; terminal leaflet — very short, very narrow, obtuse base; petiole — short.

D. Wood:

(1) *New wood.*—Color — medium green, young shoots have little or no anthocyanin coloration — green to green-bronze.

(2) *Old wood.*—Color — medium green.

E. Prickles (thorns):

(1) *Prickles.*—Present, quantity (main stalk) — ordinary. On laterals from stack — ordinary. Form — straight. Shape of upper side — concave. Shape of lower side — flat. Length — medium $\leqq 5$ mm; few $>5$ mm. Color — tan to pale pink Position — irregular.

F. Winter hardiness: Needs protection outdoors in severe climates.

I claim:

1. A new and distinct variety of rose plant of the miniature rose class, substantially as shown and described.

* * * * *

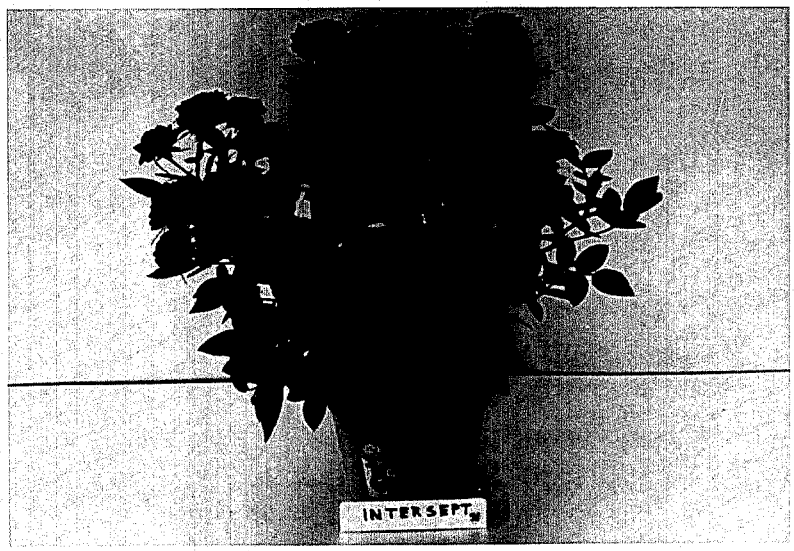
INTERSEPT

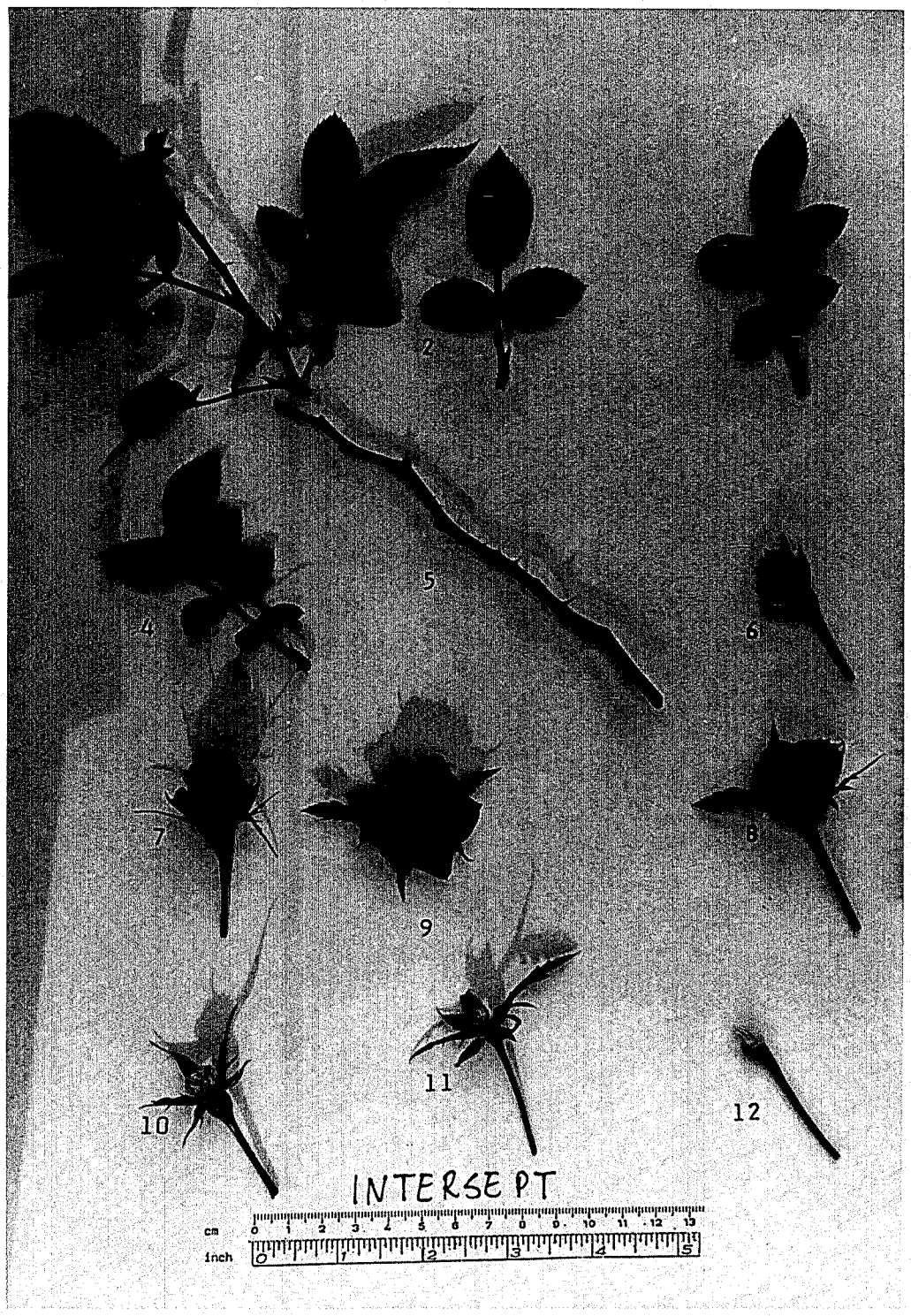
2
4
5
6
7
8
9
10
11
12
INTERSEPT
cm
inch

UNITED STATES PATENT AND TRADEMARK OFFICE

CERTIFICATE OF CORRECTION

PATENT NO. : Plant 8,349

DATED : August 17, 1993

INVENTOR(S) : G.P. Ilsink

It is certified that error appears in the above-indentified patent and that said Letters Patent is hereby corrected as shown below:

Column 3, line 2, change "45-45C" to -- 45A-45C --.

Column 4, line 8, change "acumiante" to -- acuminate --.
Column 4, line 23, change "stack" to -- stalk --.

Signed and Sealed this

Eighth Day of August, 1995

*Attest:*

*Attesting Officer*

BRUCE LEHMAN

*Commissioner of Patents and Trademarks*